US00PP14198P29

(12) United States Plant Patent
Plevier

(10) Patent No.: US PP14,198 P2
(45) Date of Patent: Oct. 7, 2003

(54) ALSTROEMERIA PLANT NAMED 'ZANTRICE'

(50) Latin Name: *Alstroemeria*
Varietal Denomination: 'Zantrice'

(75) Inventor: Franciscus B. Plevier, Sassenheim (NL)

(73) Assignee: Van Zanten Plants B.V. (NL)

( * ) Notice: Subject to any disclaimer, the term of this patent is extended or adjusted under 35 U.S.C. 154(b) by 0 days.

(21) Appl. No.: 09/640,811

(22) Filed: Aug. 16, 2000

(51) Int. Cl.[7] ..... A01H 5/00
(52) U.S. Cl. ..... Plt./309
(58) Field of Search ..... Plt./309

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new and distinct Alstroemeria plant variety producing flowers of attractive coloration.

1 Drawing Sheet

Classification: The present invention relates to a new Alstroemeria sp. plant, in the family Amaryllidaceae.

Variety denomination: The new Alstroemeria sp. plant has the varietal denomination 'Zantrice.'

BACKGROUND OF THE INVENTION

The present invention relates to a new and distinct variety of Alstroemeria, which is a hybrid resulting from a cross of two unnamed, undistributed seedlings; namely, 290–032 as seed parent and 472–011A as pollen parent. The 'Zantrice' hybrid was produced as a seedling in a research station in Hillegom, the Netherlands, and combines the flower color of the seed parent with the stem quality of the pollen parent.

Asexual reproduction by dividing rhizomes, and by tissue culture, through successive generations in Rijsenhout, the Netherlands, has demonstrated that the combination of characteristics as herein disclosed for 'Zantrice' are firmly fixed and retained through successive generations.

SUMMARY OF THE INVENTION

The new variety of Alstroemeria, 'Zantrice', produces attractive flowers.

DESCRIPTION OF ILLUSTRATION

The new variety of Alstroemeria hybrid is illustrated in the accompanying illustration, which shows typical flower characteristics of a one-year-old plant grown in a greenhouse in the Netherlands, with colors being as nearly true as is possible for illustrations of this type. The photographic illustration submitted with this Application is a detail of flower stems of the new variety.

DETAILED DESCRIPTION OF THE NEW VARIETY

The following is a detailed description of the new cultivar of Alstroemeria hybrid as observed in a greenhouse in Rijsenhout, The Netherlands. The plants described is of a 1-year old plant grown in a glass house in The Netherlands. Color designations indicated are in accordance with The Royal Horticultural Society Colour Chart by color plate designations.

'Zantrice' has not been observed under all possible environmental conditions. Phenotypic expression may vary with variations in environment such as temperature, light intensity, day length and growing and cultural conditions.

Plant:
- *Form.*—Bush.
- *Shape.*—Upright.
- *Height.*—About 140 to 180 cm.
- *Growth rate.*—Medium.
- *Time to flowering stage.*—About 80 to 100 days (from young rooted rootstocks, the stage of development in which the varieties are sold, to flowering stage in commercial greenhouse conditions).
- *Pinching.*—Not required.

Stem:
- *Main stem or cain length.*—About 160 cm.
- *Internode length.*—About 1 to 4 cm.
- *Growth.*—Vigorous.
- *Strength.*—Strong.
- *Quantity.*—About 170 to 190 harvestable stems per $m^2$.

Lateral branches:
- *Average number.*—About 170 to 190.
- *Color.*—Near 137A.
- *Length.*—About 140 to 180 cm.
- *Diameter.*—About 0.5 to 1.2 cm.
- *Texture.*—Smooth.

Foliage:
- *Quantity.*—Abundant.
- *Number of leaves.*—About 20 to 60 per stem.
- *Size of leaf.*—Length about 4.5 to 16 cm; width about 1 to 3.5 cm.
- *Shape of leaf.*—Elliptical.
- *Margin type.*—Minutely crimped.
- *Texture.*—Leathery.
- *Color.*—Upperside near 137A; underside near 137A.
- *Phyllotaxy.*—Asymmetrical single.
- *Venation pattern.*—Parallel.
- *Venation color.*—Near 143A.
- *Points of attachment.*—Sessile.

Other plant characteristics:
- *Thorns.*—No.
- *Spines.*—No.
- *Prickles.*—No.

*Bulbs.*—No.
*Corms.*—No.
*Rhizomes.*—Yes. Color: Near 155A. Size: About 15 to 35 cm.
*Disease resistance.*—Unknown.
*Fragrance.*—None.

INFLORESCENCE—FLOWER/FLORET

Blooming habit: Continuous, with no need to pinch spent umbels to maintain continuous blooming condition.
Flower bud:
*Size.*—diameter: About 1 cm. depth (or length): About 0.5–4.5 cm.
*Form or shape.*—Pearshaped; long, but not pointed.
*Rate of opening.*—Fast.
Blooms:
*Abundance.*—Blooms profusely throughout the year.
*Discoloration after full bloom.*—None.
*Effect of wet or hot weather.*—None.
*Persistence* (*do flowers hang on and dry*).—No.
Flower Size: Medium, measured at stage of development when first anthers release their pollen.
*Diameter.*—About 6 cm.
*Depth.*—About 5.5 cm.
Borne: Singly.
Shape or Form:
*Bloom first opens.*—Cup.
*Mature bloom.*—Cup.
Petalage:
*Number of petals.*—6.
*Arrangement.*—Two concentric circles of 3 petals.
*Form of tepals.*—Obovate.
*Duration of tepals.*—Stay on stem about 3 weeks.
*Texture.*—Velvety.
*Appearance.*—Leathery.
Petal Color:
*Outer petal.*—Body: Near 28A. Base: Near 28A. Reverse side: Near 28A.
*Inside petal.*—Body: Near 28A to 14A. Base: Near 14A. Reverse side: Near 28A.
*Spots.*—Outer petals (3): None. Inner lateral petals (2): About 30 to 40 spots, color near 184A. Inner medial petal: About 10 to 20 spots, color near 184A.
Tepal Color:
*When tepals first divide.*—Near 151A to 34C.
*When petals begin to unfurl.*—Near 151A to 34C.
Peduncle or Flower Stem:
*Length.*—About 1 to 4 cm.
*Color.*—Near 144A.
*Strength.*—Strong, erect.
*Upright.*—Yes.
*Hairy.*—No.
Other Flower Characteristics:
*Discoloration after full bloom.*—None.
*Effect of wet or hot weather.*—None.
*Fragrance.*—None.
*Lasting quality.*—on plant: About 3 weeks. as cut flower: About 16 to 18 days.

REPRODUCTIVE ORGANS

Stamen:
*Number.*—About 6.
*Arrangement.*—Side by side around style.
Anthers:
*Size.*—About 5 to 10 mm.
*Color.*—Near 14A.
Filaments:
*Length.*—About 30 to 40 mm.
*Color.*—Near 32C.
Pollen:
*Color.*—Near 17A.
Pistil:
*Number.*—1.
Style:
*Length.*—About 4 to 5 cm.
*Color.*—Near 30A.
Stigma:
*Color.*—Near 31A.
Fruit:
*Fertile.*—Yes.
*Shape.*—Round.
*Color at maturity.*—Near 163A.

I claim:

1. A new and distinct Alstroemeria plant of the variety substantially as shown and described.

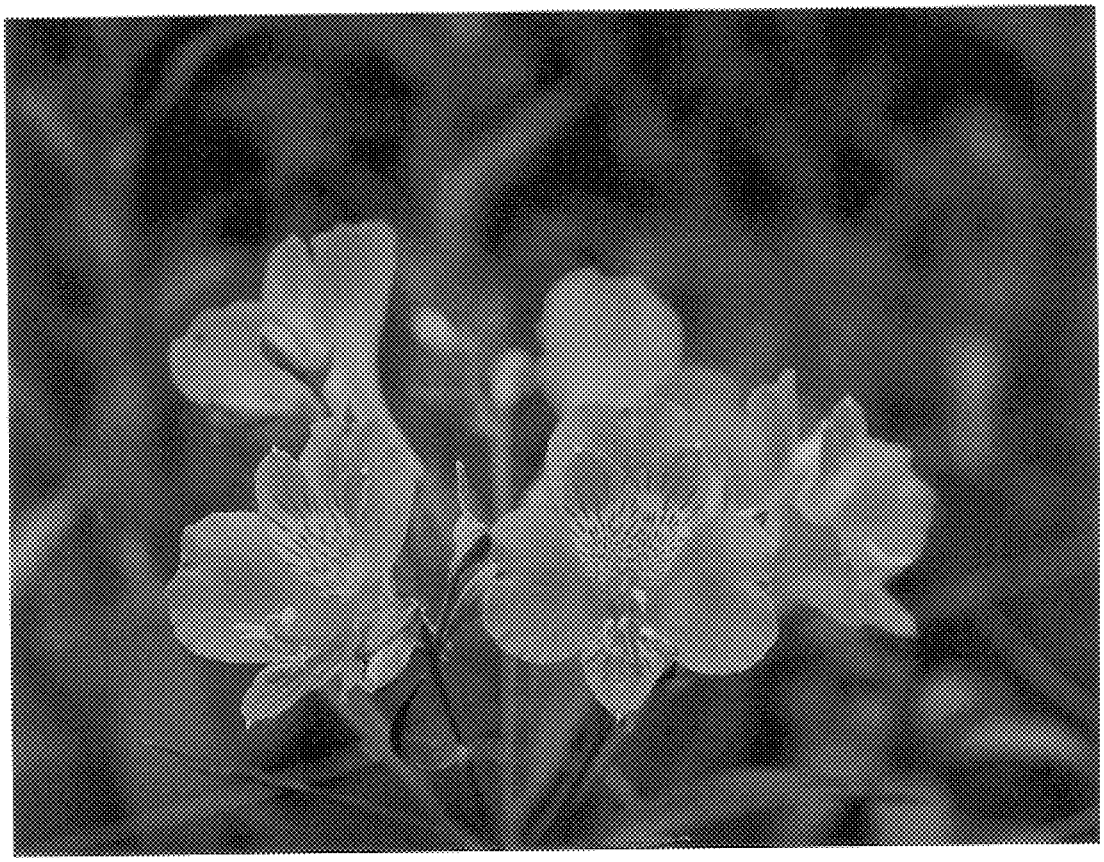

* * * * *